US005624660A

United States Patent [19]
Sharp

[11] Patent Number: 5,624,660
[45] Date of Patent: Apr. 29, 1997

[54] STRESS RESPONSE IMAGING BY DETECTION OF DECREASED PROTEIN SYNTHESIS

[75] Inventor: Frank R. Sharp, San Mateo, Calif.

[73] Assignee: The Regents of the University of California, Oakland, Calif.

[21] Appl. No.: 472,707

[22] Filed: Jun. 6, 1995

[51] Int. Cl.$^6$ .......................... A61K 51/00; A61M 36/14
[52] U.S. Cl. ........................ 424/1.65; 424/9.1; 424/9.3; 424/9.4
[58] Field of Search ................. 424/9.1, 9.2, 9.4, 424/1.11, 1.33, 1.65, 1.69, 9.323, 9.3; 530/300, 324, 325, 326, 327, 328, 329, 330; 534/10, 15

[56] References Cited

U.S. PATENT DOCUMENTS 5,330,742  7/1994  Deutsch et al. ........................ 424/9.323
5,376,356  12/1994  Morgan, Jr. ............................ 424/1.69

OTHER PUBLICATIONS

Malsey et al (1991) British J. of Clinical Practice (BJCP); vol. 45, No. 4, pp. 265–272. "Clinical Applications of Positron Emission Tomography".

Graham et al (1994), Annals of Neurology, vol. 35, No. 4, pp. 490–494 "Magnetic Resonance Spectroscopy of N-acetylaspartate in Hypoxic–Ischemic Encephalopathy".

Mies et al (1991), Journal of Cerebral Blood Flow and Metabolism, vol. 11, pp. 753–761 "Isochemic Thresholds of Cerebral Artery Occlusion in Rat".

Barkovich (1992), AJNR vol. 13, pp. 959–972 "MR and CT Evaluation of Profound Neonatal and Infantile Asphyxia".

Jacobs (Oct. 1995), Stroke, vol. 26, pp. 1859–1866 "Amino Acid Uptake in Ischemically Compromised Brain Tissue".

Tamura et al (Mar. 1995), Child's Nervous System, vol. 11, pp. 141–144, "Calcified astrocytoma of the amygdalo–hippocampal region in children".

Ronne–Engstrom (1992), Journal of Cerebral Blood Flow and Metabolism, vol. 12, pp. 873–876, "Intracerebral Microdialysis of Extracellular Amino Acids in the Human Epileptic Focus".

Kiessling, et al., *Regional Impairment of Protein Synthesis in the Rat Brain During Bicuculline–induced Seizures* (1984) 296 Brain Research 1–13.

Dwyer, et al., *Focal Protein Synthesis Inhibition in a Model of Neonatal Hypoxic–Ischemic Brain Injury* (1987) 95 Experimental Neurology 277–289.

Thilmann, et al., *Persistent Inhibition of Protein Synthesis Precedes Delayed Neuronal Death in Postischemic Gerbil Hippocampus* (1986) 71 Acta Neuropathol (Berl) 88–93.

Krause, et al., *Suppression of Protein Synthesis in the Reperfused Brain* (1993) 24:5 Stroke 747–756.

Ishimaru, et al., *Ischemic Thresholds of Cerebral Protein Synthesis and Energy State Following Middle Cerebral Artery Occulsion in Rat* (1991) 11 Journal of Cerebral Blood Flow and Metabolism 753–761.

Medline Database Search Results on Heat Shock, Brains and Ischemia.

Primary Examiner—John Kight
Assistant Examiner—Dameron L. Jones
Attorney, Agent, or Firm—Townsend and Townsend and Crew LLP

[57] ABSTRACT

Physiological conditions in a subject which result in a reduction in the rate of protein synthesis are detected by the administration of a labeled amino acid, followed by imaging of the subject's body to detect the uptake of the labeled amino acid in protein synthesis. The method is particularly useful as applied to the detection of ischemic events, focal or global, as well as hypoglycemia and status epilepticus.

12 Claims, 4 Drawing Sheets ns, 5,624,660

STRESS RESPONSE IMAGING BY DETECTION OF DECREASED PROTEIN SYNTHESIS

This invention resides in the area of medical diagnoses, and in particular to diagnostic methods for various physiological conditions including ischemia, hypoglycemia, and status epilepticus.

BACKGROUND OF THE INVENTION

Certain physiological conditions which occur prior to more serious and permanent conditions or injuries are either not susceptible to detection or are detectable only on pathological specimens. Ischemia, for example, is a localized tissue anemia resulting from obstruction of the blood supply or from vasoconstriction. If sustained, ischemia can result in infarction which is detectable by various known scanning techniques. There is no known method of detecting ischemia short of infarction, however. Similarly, neuronal cell loss may be indicative of an underlying abnormality which can lead to infarction, but methods for detecting infarction may not show the extent of the areas of neuronal loss. The detection of both focal and global ischemia, neuronal loss and other pre-infarction conditions would serve to identify and localize the underlying abnormality and permit early treatment. Similar benefits would be achieved for such conditions as hypoglycemia, status epilepticus, and other types of stress or cell injury in brain and all other organs.

SUMMARY OF THE INVENTION

It has now been discovered that the occurrence of conditions such as ischemia, hypoglycemia and status epilepticus can be detected in a localized manner by determining abnormal decreases in protein synthesis as indicated by decreases in amino acid uptake (i.e., consumption by reaction with other amino acids in protein synthesis). The rate of amino acid uptake is determined by the use of labeled amino acids, followed by imaging of the patient or a portion of the patient's body with conventional imaging technology appropriate for the particular label. A variety of known labeling technologies and particular labels can be used, as can a variety of known imaging technologies. The labeled amino acids can be administered in the same manner as contrast agents which are conventionally administered for other, currently used imaging methods.

These and other features and advantages of the invention will be better understood from the description which follows.

DETAILED DESCRIPTION OF THE INVENTION AND PREFERRED EMBODIMENTS

Figure 1:
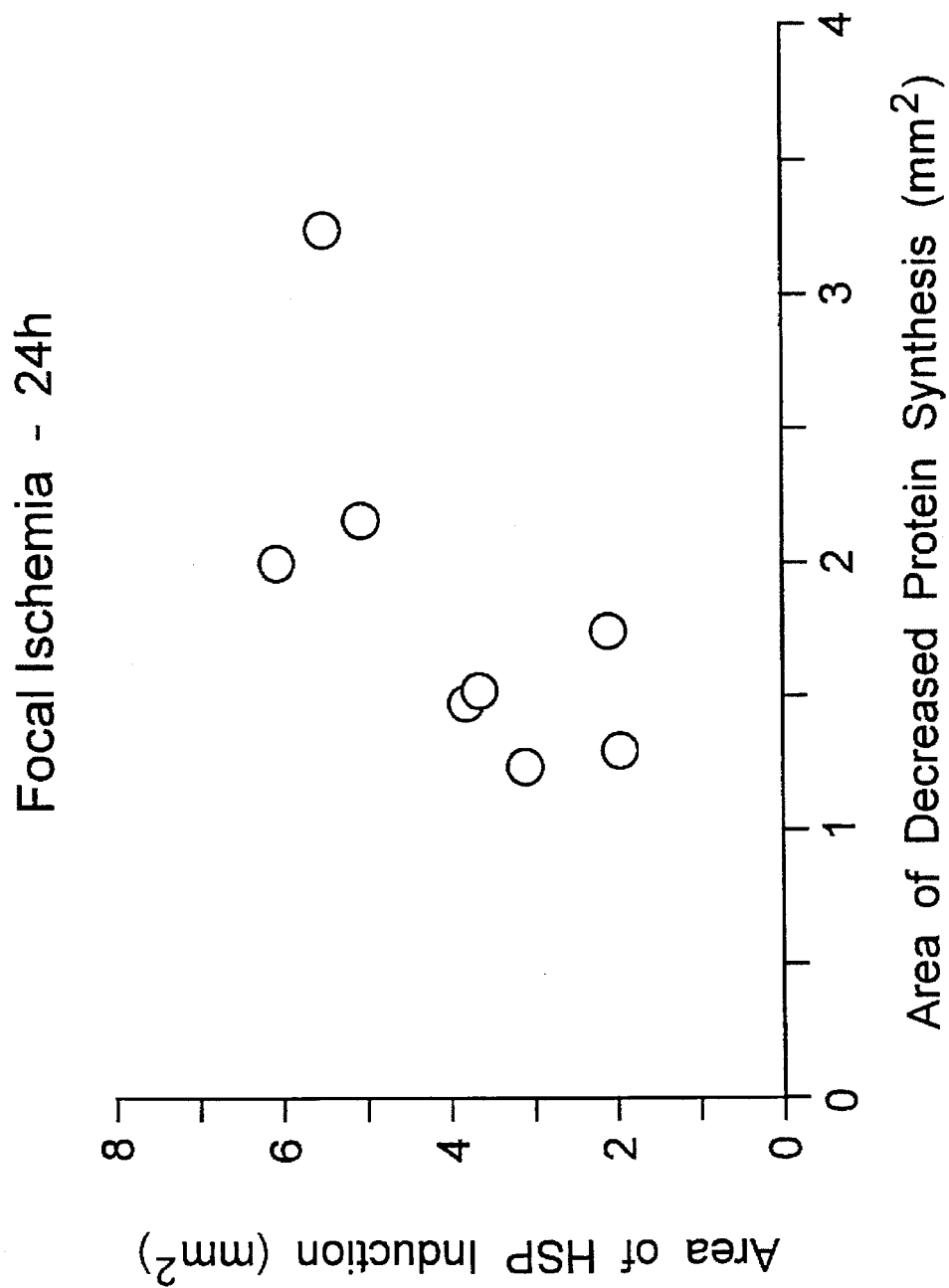
FIG. 1 is a plot of the size of areas where increased induction of the heat stress protein HSP70 was observed in an induced focal ischemia experiment after 24 hours vs. the size of areas of decreased protein synthesis in the same experiment.

Stress injuries result in localized physiological changes, some of which are transient. Included among these are the induction of the heat shock protein HSP70 and a decrease in protein synthesis in general. In many cases, the spatial boundaries of the affected areas of these two effects are the same, while in others the spatial boundaries differ, but the affected areas occur in the same tissue or the same region of a particular tissue. Thus, decreases in protein synthesis correlate well with tissues which have undergone stress injuries or cellular injuries of any type.

In accordance with the present invention, decreases in protein synthesis are detected by decreases in amino acid consumption, using labeled amino acids. Any of the amino acids, or analogs of these amino acids, can be used. The common amino acids are glycine, L-alanine, L-valine, L-isoleucine, L-leucine, L-serine, L-threonine, L-proline, L-aspartic acid, L-glutamic acid, L-lysine, L-arginine, L-asparagine, L-glutamine, L-cysteine, L-methionine, L-tryptophan, L-phenylalanine, L-tyrosine, and L-histidine. Preferred among these, for purposes of the present invention, are L-leucine (leucine), L-cysteine (cysteine), L-methionine (methionine), and L-tyrosine (tyrosine). Leucine is particularly preferred.

Labeling of the amino acid can be achieved by attaching a detectable label either by covalent linkage, an affinity-type bond, or chelation, provided that the label does not interfere with the ability of the amino acid to enter into protein synthesis. Labels of particular interest include radioactive labels and paramagnetic labels. Radioactive labels can include any of the following:

monovalent radionuclides, aliphatic, alicyclic and aromatic groups containing monovalent radionuclide substituents, aliphatic, alicyclic and aromatic groups containing polyvalent radionuclide substituents, and radionuclide conjugates, including chelates of radionuclides and other ligand-bonded radionuclide structures.

Paramagnetic labels are primarily conjugates of paramagnetic elements, the conjugates being chelates or other ligand-bonded structures.

Examples of aliphatic groups are alkyl groups such as straight-chain $C_1$–$C_4$ alkyls; examples of alicyclic groups are saturated $C_5$–$C_7$ cycloalkyls; and the primary example of an aromatic group is a phenyl group. Depending on its valence, the label may either be a substitute for a carbon or hydrogen atom or a link in an otherwise carbon chain in an alkyl, alicyclic or aromatic structure.

For embodiments in which the label is attached to the amino acid as a chelate, the chelating ligand may be any of the wide variety of such ligands well known among those in nuclear medicine and chelate chemistry. Examples of chelating ligands are diethylenetriamine pentaacetic acid (DTPA), ethylenediamine tetraacetic acid, nitrilotriacetic acid (NTA), and ethylene glycol-bis(β-aminoethyl ether)-N,N-tetraacetic acid. Examples of ligands to which the label can be conjugated are diamino dimercaptide and hydrazinonicotinamide. The derivatization and attachment of these ligands to the amino acid are matters of routine chemistry well known among those skilled in the art.

Examples of radioactive labels are $^{11}C$, $^{14}C$, $^{35}S$, $^{121}I$, $^{122}I$, $^{123}I$, $^{124}I$, $^{125}I$, $^{131}I$, $^{74}Br$, $^{75}Br$, $^{76}Br$, $^{77}Br$, $^{34m}Cl$, $^{18}F$ or $^{211}At$, and chelates of (or ligands bearing) $^{99m}Tc$, $^{111}In$, $^{113m}In$ and $^{67}Ga$. Among these, $^{11}C$, $^{14}C$, $^{35}S$, and $^{18}F$ are particularly preferred.

Of the paramagnetic metals, a wide range are known and suitable for the present invention. These metals have atomic numbers of 22–29 (inclusive), 42, 44 and 58–70 (inclusive), and have oxidation sates of 2 or 3. Those having atomic numbers of 22–29 (inclusive) and 58–70 (inclusive) are preferred, and those having atomic numbers of 24–29 (inclusive) and 64–68 (inclusive) are more preferred. Examples of such metals are chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III). Chromium (III), manganese (II), iron (III) and gadolinium (III) are particularly preferred.

Suitable imaging methods include positron emission tomography (PET), single-photon emission computed tomography (SPECT), and magnetic resonance (MR). Localized decreases in protein synthesis will appear as regions of low, decreased or absent signals, since the labeled amino acid will not be retained in regions where protein synthesis is not occurring or is occurring at a depressed rate.

The labeled amino acid is administered to a patient by conventional procedures which have previously been used for the administration of contrast agents for conventional imaging. Aqueous solutions of the labeled amino acids are most conveniently used. The concentrations of the labeled amino acids in these solutions and the amounts administered may vary widely, the optimum in each case varying with the specific activity of the label, the method of administration, the strength of signal desired or needed, and the age, weight and condition of the patient or subject to whom administration is made. In most cases, best results are obtained with solutions at concentrations of about 0.05 to about 2.0 moles of the labeled amino acid per liter, preferably about 0.1 to about 1.0 mole per liter. Likewise, best results in most cases are usually obtained with dosages ranging from about 0.01 to about 1.0 millimole of agent per kilogram of whole body weight (mM/kg), preferably from about 0.05 to about 0.5 mM/kg. Administration may be achieved by any parenteral route and method, most notably by intravenous administration. The rate of administration may likewise vary, best results generally being obtained at rates ranging from about 0.1 mM/min/kg to about 1.0 mM/sec/kg.

Administration of the labeled amino acid can be made from as early as a few minutes after the event suspected of involving a stress or cell injury to as late as days or weeks after the event. Imaging can then be performed after a sufficient period of time to permit a measurable amount of uptake of the amino acid by protein synthesis. This period of time may be as early as thirty minutes after administration of the amino acid, or after a longer period of time, such as two hours, four hours, 24 hours, or up to several days. Intervals ranging from about 1 hour to about 24 hours are preferred, and intervals ranging from about 1 hour to about 4 hours are most preferred. A two-hour interval is particularly preferred.

The method of this invention is of primary interest as applied to human subjects, but will be applicable to animal subjects in general, particularly mammalian animals. The entire body of the subject may be imaged, or only a portion of the body or a single organ, such as the brain, heart, lung, liver, or kidney. Methods for focusing on individual organs are the same as those used by the same imaging methods for conventional imaging procedures.

Conditions which can be detected by the method of the present invention include any conditions which result in a decrease or stoppage in the rate of protein synthesis. Examples are transient ischemia events of the brain or any other organ of the body, focal ischemia within the brain or other organ, hypoglycemia of the brain or other organ, global ischemia of the brain or other organ, and status epilepticus.

The following examples are offered for purposes of illustration only, and are not intended to limit or define the invention in any manner.

EXAMPLES

Methods

Three types of neuronal injury—focal ischemia, global ischemia, and status epilepticus—were produced in test animals as follows.

Focal ischemia of the middle cerebral artery.

Adult Sprague Dawley rats (240–260 g) were anesthetized with chloral hydrate. The carotid was isolated and its major branches ligated including the external carotid and pytergopalatine. A 4-0 nylon suture, blunted at the tip, was threaded into the stump of the external carotid up into the internal carotid to the middle cerebral artery bifurcation (22 mm). The suture was left in position for a period of 30 minutes, after which time the suture was removed, the external carotid ligated and the wounds sutured. (Ischemia for 30 minutes is generally known in the art to produce infarction of the lateral striatum but does not produce cortical infarction.) Brain temperature was maintained in the range of 37.5° C.±0.2 with a heating lamp throughout the procedure and until the animals recovered. The animals recovered within one hour.

Global ischemia.

Gerbils of both sexes were anesthetized with isoflurane and the carotids rapidly isolated. Anesthesia was discontinued and the carotids occluded for either 5 or 10 minutes using vascular clamps. The clamps were then removed and the wounds sutured. Body temperature was maintained in the range of 37.5° C.±0.2 with a heating lamp throughout the procedure. The animals recovered within one hour. Ischemia for 5 and 10 minutes is known in the art to generally produce delayed death of most CA1 pyramidal hippocampal neurons.

Status epilepticus.

Adult Sprague Dawley rats of both sexes were given kainic acid (10 mg/kg) intraperitoneally. Only subjects that exhibited wet dog shakes, trembling and other evidence of limbic seizures, or subjects that had generalized convulsions were studied. These seizures are known to produce significant cell death in piriform cortex and in the CA1 and CA3 pyramidal neurons of the hippocampus as well as many other regions. In this test, seizures of all such subjects stopped within an hour.

Following focal ischemia, global ischemia and status epilepticus, all subjects were observed for at least one hour or until they recovered fully. All subjects were then returned to their home cages where food and water were available ad libitum up to the time of sacrifice. Tests were then performed as follows.

Regional Protein Metabolism.

The subjects were injected with $^{35}S$ methionine, $^{35}S$ cysteine or $^{14}C$ leucine intraperitoneally (50 µCi/100 g body weight) at either 4, 24 or 48 hours following the injury, then sacrificed two hours later. Most subjects were anesthetized with isoflurane and ketamine (100 mg/kg) and then perfused through the ascending aorta with 0.9% saline (200 cc) followed by 4% paraformaldehyde in 0.1 M pH 7.4 phosphate buffered saline. Brains were removed and sectioned on a vibratome (50 μm thick). Sections were immunostained for HSP70 as described below and mounted on gelatinized slides and dried. Dried slides of perfused brain were exposed to film (Kodak SB5 autoradiography film) for an appropriate period in x-ray cassettes with standards. Films were developed and analyzed as described below. For a few subjects, regional protein synthesis was calculated using published equations for leucine (Smith, C.B., et al., *J. Neurosci.* 4:2489–2496 (1984); Sun, Y., et al. *J. Neurochem.* 59:863–873 (1992)).

A few experiments were performed to show that the patterns of radioactivity in fresh frozen sections were the same as those obtained from perfusion fixed sections. Following focal ischemia, global ischemia and status epilepticus, subjects were anesthetized with isoflurane, decapitated, and the brains removed and frozen. Following embedding, these brains were cut on a cryostat at −20° C. and sections picked open onto gelatinized slides and dried. These sections were autoradiographed on x-ray film as described above.

Immunocytochemistry and Nissl staining.

Perfusion-fixed brain sections cut on a vibratome were placed in PBS (0.1 M pH 7.4 phosphate buffered saline). This was followed by immersion in 10% serum/1% BSA/0.1% Triton X-100. The sections were then incubated overnight at 4° C. in a first antibody which was mouse monoclonal anti-human HSP70 antibody (C92, Amersham Corporation, Arlington Heights, Ill., USA) diluted 1:4000. After three ten-minute washes in PBS, the sections were incubated for two hours in sheep anti-mouse IgG antibody (1:200, Amersham). The sections were then washed three times in PBS, then incubated in avidin-biotin-horseradish peroxidase complex (Vector Laboratories, Inc., Burlingame, Calif., USA), followed by 0.015% diaminobenzidine and 0.001% hydrogen peroxide. The sections were then washed and dried. Control sections were incubated without the first antibody and showed no staining. The C92 monoclonal to HSP70 has been shown in the prior art to immunostain human and rat HSP70 and to stain the protein product of the rat HSP70 cDNA.

Once the immunocytochemistry was completed, the dried slides were placed in x-ray cassettes and covered with Kodak SB5 autoradiographic film. Once the autoradiography was completed, each section was Nissl stained to determine whether them was any evidence of infarction which could then be compared to regions of decreased protein synthesis and to regions of HSP70 protein induction.

Regional Comparisons of Areas of Decreased Protein Synthesis and Areas of Increased HSP70 Induction.

A visual comparison was made between the regions of HSP70 induction and the regions of decrease in total protein synthesis. Quantitation of the areas was performed by use of a computer-based imaging system. A density threshold was set so that the computer would detect either the region of decreased protein synthesis or the region of HSP70 induction. The areas of total protein synthesis and the areas of HSP70 induction were then measured in each hemisphere in the same selected regions of cortex from the same slide from animals in each group.

Results

Focal Ischemia.

Visual observation of the autoradiographic scans indicated that protein synthesis was virtually absent in areas of striatal infarction at 24 hours and 48 hours after the thirty minutes of focal ischemia in the middle cerebral artery. Protein synthesis was markedly decreased but not absent in areas of cortex in the middle cerebral artery at 4 hours, 24 hours, and 48 hours after the ischemia. The decreased protein synthesis in cortex often occurred in a laminar pattern and almost always involved superficial layers 2 and 3 of cortex, either in a continuous manner or a patchy manner. Protein synthesis was also decreased in deeper layers 5 and 6 in some subjects, the decrease being either continuous or patchy. The decrease in protein synthesis was most apparent at 4 hours, but was still quite apparent at 24 hours and 48 hours following the middle cerebral artery ischemia. In one subject, the middle cerebral artery ischemia did not produce striatal or cortical infarction but did result in decreased protein synthesis 24 hours later throughout the striatum and cortex in the middle cerebral artery distribution.

Comparison of the cortical regions in which protein synthesis was decreased following middle cerebral artery ischemia to the cortical areas in which HSP70 immunostaining occurred showed a definite correlation between the two. The areas of HSP70 induction and the areas of decreased protein synthesis were confined mainly to the superficial cortical layers. There was some HSP70 induction in deeper layers in an area where protein synthesis did visibly decrease. This was the pattern in most subjects where the areas of HSP70 induction were always much larger than the areas of decreased protein synthesis. The HSP70 induction in cortex following middle cerebral artery ischemia was localized almost exclusively to neurons located usually in layers 2 and 3 and less often in layers 5 and 6.

The Nissl staining showed that the thirty minutes of focal ischemia produced infarction in the lateral striatum or throughout the entire striatum 24 and 48 hours later in almost every subject. In many subjects the infarctions extended into the adjacent hypothalamus and edges of thalamus. No cortical infarctions were observed in any of these subjects.

Global ischemia.

One day following five minutes of global ischemia, protein synthesis was near zero in the CA1 region of the hippocampus, which is the region where neurons will die. Protein synthesis appeared normal at this time in the CA3 regions and dentate gyrus of hippocampus and in all layers of cortex.

Ten minutes of global ischemia produced a different pattern of protein synthesis. At tour hours following the ischemia, protein synthesis was decreased throughout all layers of neocortex, though the reductions were greatest in the superficial layers. Protein synthesis was also decreased in the hippocampus, particularly CA1 in some subjects. By 24 hours after the ischemia, protein synthesis was decreased in superficial layers of the neocortex bilaterally. Protein synthesis was near zero in the CA1 regions of hippocampus bilaterally, although protein synthesis was near normal in the CA3 regions and dentate gyrus.

Comparisons of the areas of decreased protein synthesis following the global ischemia with the areas of HSP70 induction showed that the decreased protein synthesis occurred in the superficial layers of cortex and the HSP70 induction occurred in the superficial layers of cortex. The total region of HSP70 induction correlated extremely well with the total area of decreased protein synthesis. The HSP70 induction in the cortex following global ischemia was localized almost exclusively to neurons.

No infarction was observed in the brains of the gerbils subjected to global ischemia. Death of CA1 neurons was detected using Nissl stains as early as 24 hours and which was more apparent at 48 hours following the 10 minute global ischemia.

Kainic Acid Status Epilepticus.

Many, although not all, of the animals injected with kainic acid displayed evidence of necrosis of the tips of the temporal lobes, the necrosis associated with the absence of protein synthesis. In addition, decreased or absent protein synthesis was observed in CA3 neurons in the hippocampus. These neurons are known to die following kainic acid-induced seizures.

Protein synthesis was decreased in thin laminae in the neocortex in most subjects at 24 hours and 48 hours following the seizures. These laminae of decreased protein synthesis correlated with laminae of HSP70 induction. The HSP70 induction following kainic acid seizures was localized entirely to cortical neurons. While the highest concentrations of HSP70 neurons were in superficial layer 5, stained neurons were also detected in deep parts of layer 3, superficial layer 2 and deep portions of layer 6. Therefore, the decreased protein synthesis correlated with the regions of highest densities of HSP70 immunoreactive neurons. Nissl stains demonstrated that there was no infarction in neocortex in any animal.

Relationship between areas of decreased protein synthesis and areas of HSP70 induction.

Figure 2:
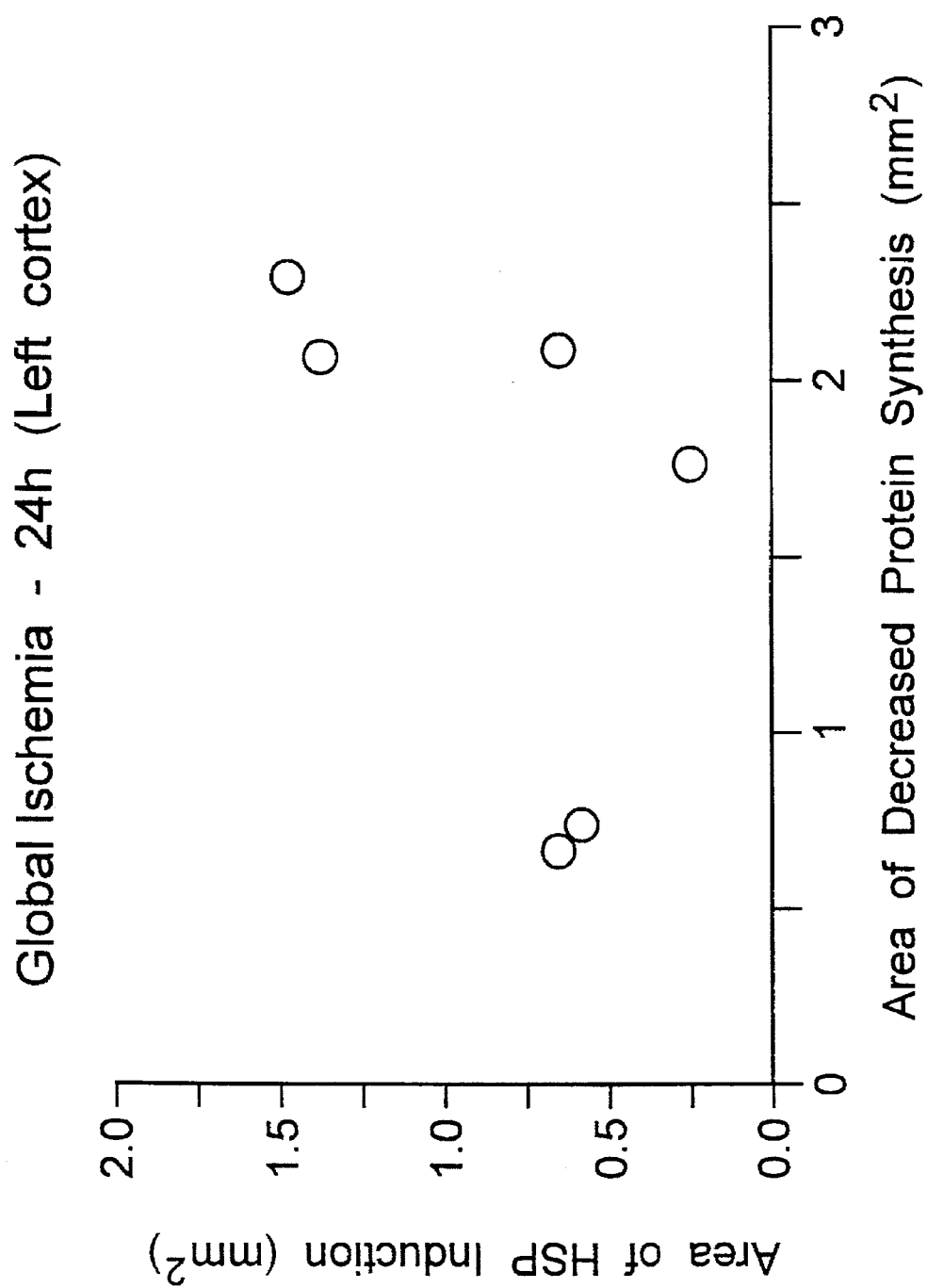
FIG. 2 is a plot analogous to that of FIG. 1, except that the stress event was created by induced global ischemia in the left cortex.
Figure 3:
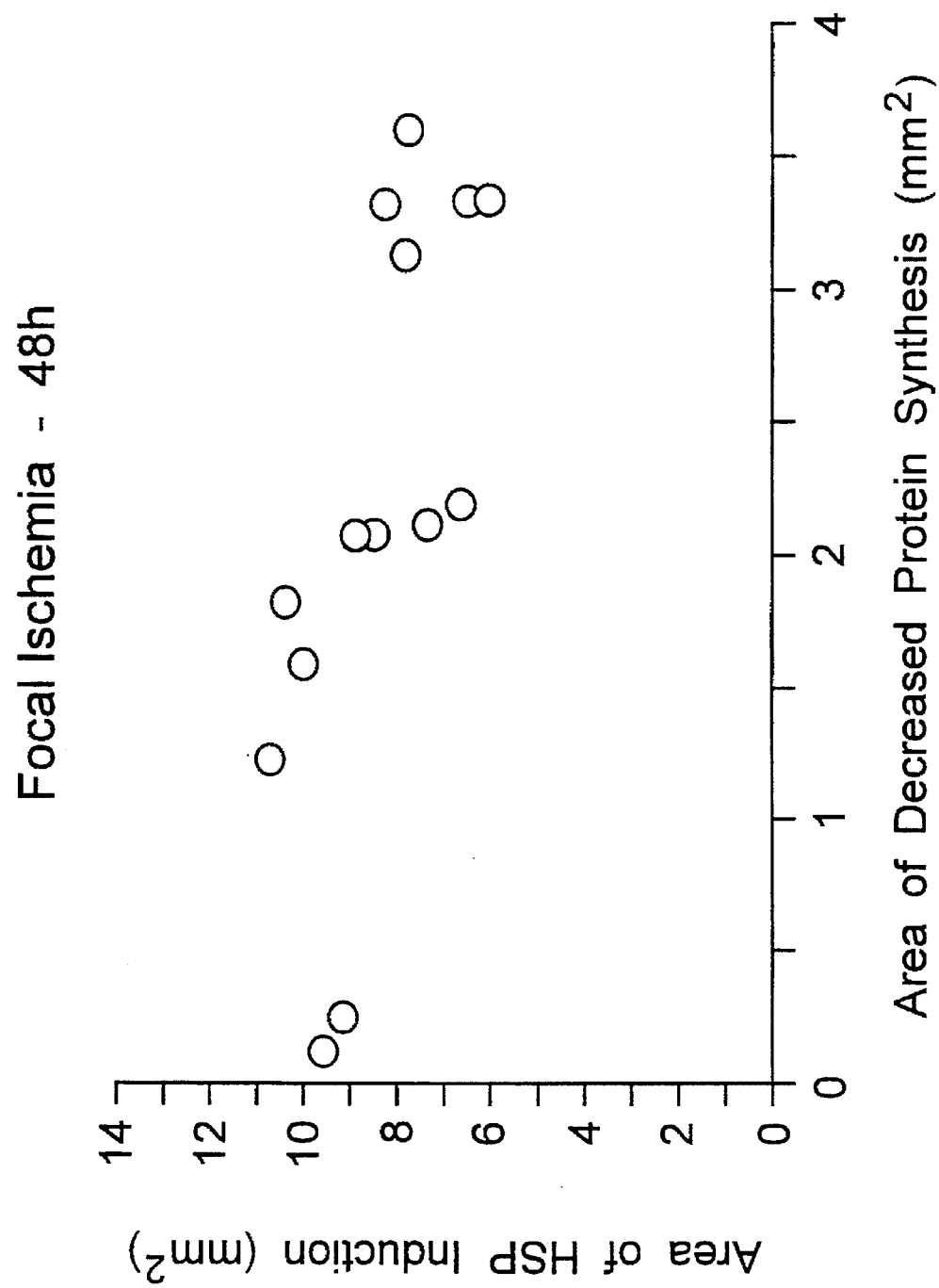
FIG. 3 is a plot analogous to that of FIG. 1, except that the observations were made at 48 hours.
Figure 4:
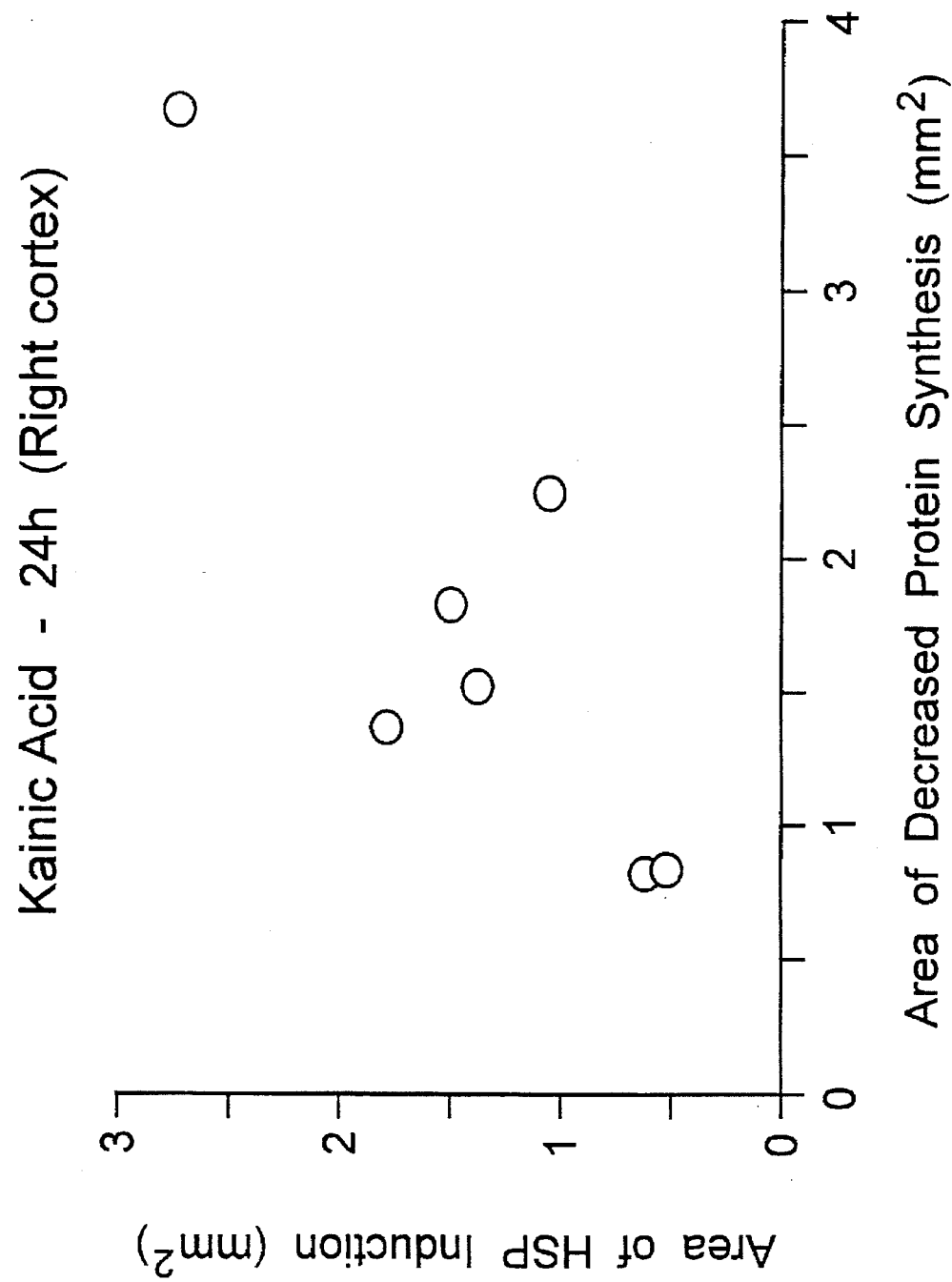
FIG. 4 is a plot analogous to that of FIG. 1, except that the stress event was created by kainic acid injection in the right cortex.

FIGS. 1, 2, 3, and 4 demonstrate the relationship between the areas of decreased protein synthesis (horizontal axis) and the areas of HSP70 induction (vertical axis) in one neocortex on multiple sections from single subjects. Note that the areas of HSP70 induction were usually greater than the areas of decreased protein synthesis particularly for focal ischemia (FIGS. 1 and 3), whereas the areas of HSP70 induction and decreased protein synthesis were more similar in size following global ischemia and seizures (FIGS. 2 and 4). For some of the subjects there appeared to be a distinct correlation between the size of the areas of HSP70 induction and the areas of decreased protein synthesis following focal ischemia (FIG. 1), global ischemia (FIG. 2) and seizures (FIG. 4).

However, in some of the subjects there was no correlation between the areas of HSP70 induction and decreased protein synthesis (FIG. 3). In these subjects some decrease of protein synthesis occurred but this did not correlate with the area of the HSP70 induction. The areas in which the protein decreases occurred were always centered over areas of the HSP70 induction. Even though the areas of induction did not correlate, the topography of the induction always correlated in every animal in every section. Specifically, whenever a decrease of conical protein synthesis was detected, whether it be the result of focal ischemia, global ischemia or seizures, there was always evidence of HSP70 in the same region of cortex on the same section. The opposite was not true, however. There were often regions of low level HSP70 induction in the deep cortical layers where decreases of protein synthesis could not be detected.

Correlation between perfusion-fixed and fresh frozen tissue.

Autoradiographs were compared for subjects in which focal ischemia had been produced and which were sacrificed 24 hours later. The sections of brains that had been perfusion-fixed were compared to the autoradiographs of sections of brains of subjects that had been anesthestized and decapitated and from which fresh frozen sections were prepared. The autoradiographs were nearly identical. In addition, the sections of animals for which fresh frozen sections had been prepared were fixed and re-autoradiographed. The two sets of sections were nearly identical. This indicates that the autoradiographs obtained with perfusion-fixed brains would be very similar to those obtained from fresh frozen brains, which in turn would be similar to images that could be obtained using in vivo external imaging methods.

Conclusion

These experimental results show that protein synthesis is decreased in areas of cortex which are injured but not infarcted following focal ischemia, global ischemia and kainic acid-induced status epilepticus, and that these decreases correlate with regions of hsp70 heat shock protein synthesis induction. These areas represent regions of extreme cellular stress. Decreases in protein synthesis can be detected as early as 4 hours and for as long as 72 hours after ischemia and seizures, and serve as a means of imaging the stress response in human brain in areas of the brain and other tissues of the body that are injured but not infarcted.

The following are hypothetical case examples of clinical situations illustrating the use of stress response imaging of human subjects in accordance with the present invention.

Case No. 1.

A patient experiences an acute onset of left-sided numbness and weakness which lasts two hours, then resolves. The neurological examination and magnetic resonance imaging (MRI) of the brain are normal the next day. Stress response imaging in accordance with the present invention would be performed one day after the numbness and weakness, by administering either $^{18}F$ methionine, $^{18}F$ cysteine or $^{11}C$ leucine, or methionine, cysteine or leucine labeled with a paramagnetic metal ion such as gadolinium. The brain would then be imaged by positron emission tomography (PET), single-photon emission computed tomography (SPECT) or magnetic resonance (MR), and the resulting image would show decreased protein synthesis in the distribution of the middle cerebral artery. This would prove that the brain had been ischemic one day earlier and would confirm the diagnosis of a transient ischemic attack of the brain. There are no other tests currently available to diagnose a transient ischemic attack.

Case No. 2.

A patient experiences an acute onset of chest pain and shortness of breath. A pulmonary embolus is suspected because the patient had been at bed rest following a broken leg and casting. Pulmonary perfusion and ventilation scans and a pulmonary angiogram performed one day after the event fail to indicate any abnormalities. Stress response imaging (SRI) in accordance with the invention would then be performed as in Case No. 1 above. The SRI scan would show evidence of decreased protein synthesis in a large segment of the lung which had been ischemic on the preceding day but which had not infarcted. There is no other test currently available to diagnose an ischemic lung which had not infarcted.

Case No. 3.

A patient experiences recurrent chest pain following walking, but had not had a prior heart attack. A thallium scan of the heart was performed, and the results were equivocal. Stress response imaging in accordance with the invention would then be performed as in Case No. 1 above. The SRI scan following a particularly hard day of walking would show decreased protein synthesis in the areas of ischemic heart perfused by the ischemic heart vessel in question. Moreover, the SRI scan could be performed one day following a treadmill test and would show the same effect. The SRI scan would therefore complement thallium scanning of the heart which is currently performed to document cardiac ischemia without infarction.

Case No. 4.

A patient experiences an acute onset of left hand weakness. One day later a MRI scan shows a small lesion in the basal ganglia. A SRI scan in accordance with the invention as in Case No. 1 above, however, shows decreased protein synthesis in the entire distribution of the middle cerebral artery. This would indicate that this patient's problem was one of the heart or carotids, and not related to small vessel disease in the brain. This would suggest that the patient should either be anticoagulated for an underlying heart problem, or should have carotid surgery for carotid stenosis.

The foregoing is offered primarily for purposes of illustration. It will be readily apparent to those skilled in the art that the methods of administration, analytical procedures, and other parameters of the system described herein may be further modified or substituted in various ways without departing from the spirit and scope of the invention.

We claim:

1. A method for determining whether a subject has undergone a transitory occurrence of one or more conditions selected from ischemia, hypoglycemia, and status epilepticus, without infarction, said method comprising:

(a) administering to said subject an amino acid labeled with a detectable label in an amount sufficient to be detectable by an imaging technique; and (b) imaging said subject or a portion of said subject at least about thirty minutes after (a) to detect any localized decrease in concentration of said detectable label as an indication of a decrease in protein synthesis and therefore an indication of said occurrence and the location of such occurrence.

2. A method in accordance with claim 1 in which said detectable label is a member selected from the group consisting of radioactive labels and paramagnetic labels.

3. A method in accordance with claim 1 in which said detectable label is a radioactive label selected from the group consisting of $^{11}C$, $^{14}C$, $^{18}F$, and $^{35}S$.

4. A method in accordance with claim 1 in which said detectable label is a paramagnetic label selected from the group consisting of elements having atomic numbers of 22–29 and 58–70.

5. A method in accordance with claim 1 in which said detectable label is a paramagnetic label selected from the group consisting of chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III).

6. A method in accordance with claim 1 in which said detectable label is a paramagnetic label selected from the group consisting of chromium (III), manganese (II), iron (III), and gadolinium (III).

7. A method in accordance with claim 1 in which said amino acid is a member selected from the group consisting of leucine, tyrosine, methionine and cysteine.

8. A method in accordance with claim 1 in which said amino acid is leucine.

9. A method in accordance with claim 1 in which (b) is performed at an interval of about 1 hour to about 24 hours after (a).

10. A method in accordance with claim 1 in which (b) is performed at an interval of about 1 hour to about 4 hours after (a).

11. A method in accordance with claim 1 in which (b) comprises imaging said subject or a portion of said subject by a technique selected from the group consisting of positron emission tomography, single-photon emission computed tomography, and magnetic resonance.

12. A method in accordance with claim 1 in which (b) is performed after an interval of 24 hours or greater after (a).

* * * * *

UNITED STATES PATENT AND TRADEMARK OFFICE
CERTIFICATE OF CORRECTION

PATENT NO. : 5,624,660
DATED : April 29, 1997
INVENTOR(S) : Frank R. Sharp

It is certified that error appears in the above-identified patent and that said Letters Patent is hereby corrected as shown below:

In column 1, at line 9, insert the paragraph:
--This invention was made with Government support under Grant No. NS28167, awarded by the National Institutes of Health. The Government has certain rights in this invention.--

Signed and Sealed this

Thirtieth Day of May, 2000

Attest:

Q. TODD DICKINSON

*Attesting Officer*  *Director of Patents and Trademarks*